United States Patent [19]

Bayha et al.

[11] Patent Number: 4,556,475
[45] Date of Patent: Dec. 3, 1985

[54] ELECTROCHEMICAL GAS SENSOR PROBE CONSTRUCTION

[75] Inventors: Kurt Bayha, Oberriexingen; Helmut Weyl, Schwieberdingen, both of Fed. Rep. of Germany

[73] Assignee: Robert Bosch GmbH, Stuttgart, Fed. Rep. of Germany

[21] Appl. No.: 628,454

[22] Filed: Jul. 6, 1984

[30] Foreign Application Priority Data

Jul. 29, 1983 [DE] Fed. Rep. of Germany ....... 3327397

[51] Int. Cl.$^4$ .............................................. G01N 27/46
[52] U.S. Cl. ................................. 204/427; 204/428; 339/183; 174/75 R; 174/84 S; 174/88 S
[58] Field of Search ................................ 204/421–429; 174/75 R, 84 R, 84 S, 88 R, 88 S; 339/182, 183

[56] References Cited

U.S. PATENT DOCUMENTS

| | | | |
|---|---|---|---|
| 950,107 | 2/1910 | Larsson | 339/183 |
| 2,183,911 | 12/1939 | Howell | 339/183 |
| 2,703,393 | 3/1955 | Bird | 339/183 |
| 2,755,452 | 7/1956 | Rogiz | 339/183 |
| 3,045,078 | 7/1962 | Frantz et al. | 339/183 |
| 3,225,155 | 12/1965 | Duncan | 339/183 |
| 3,536,869 | 10/1970 | Renshaw | 339/183 |
| 4,035,613 | 7/1977 | Sagawa et al. | 219/543 |
| 4,155,827 | 5/1979 | Maurer et al. | 204/428 |
| 4,357,526 | 11/1982 | Yamamoto et al. | 219/544 |

FOREIGN PATENT DOCUMENTS 0056837 8/1982 European Pat. Off. ............ 204/428

Primary Examiner—T. Tung
Attorney, Agent, or Firm—Frishauf, Holtz, Goodman & Woodward

[57] ABSTRACT

A gas measurement probe has a casing (11) equipped with a closure shell (17) on its end away from the gas to be measured. At the other end of the casing, within its longitudinal bore, a sensor element (24) is held fast and tight in the casing. A rod-shaped part carrying a heater element fits within the sensor element and extends out of it at its end away from the gas to be measured to an extremity near which contact areas are provided on its periphery. On these contact areas, resilient connection wires lie under mechanical bias. These wires, between the loops bearing against the contact surface and their ends are bent in Z or sinuous shape so as to secure them against pulling, twisting and shaking forces. These connection elements and also another conductor running in the probe cooperate with an indexing feature of the rod-shaped element, such as a suitable groove to secure the rod-shaped component against twisting. This construction is particularly suitable for probes utilizing a solid electrolyte tubular sensor element closed at its tip.

13 Claims, 2 Drawing Figures

U.S. Patent   Dec. 3, 1985   4,556,475
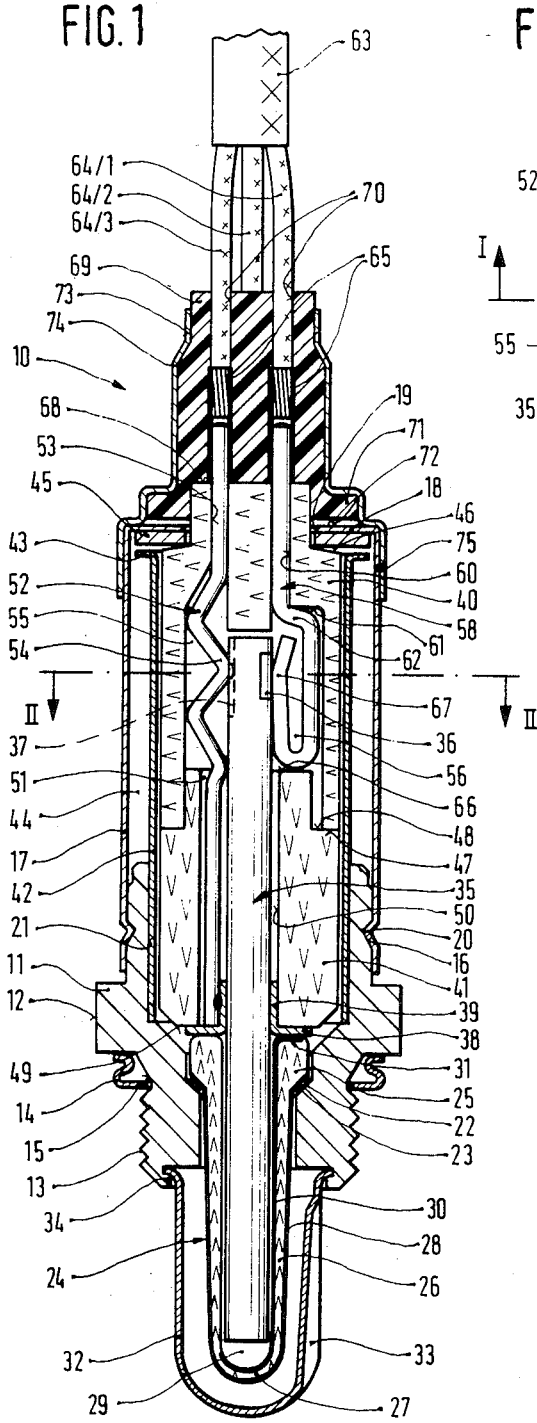
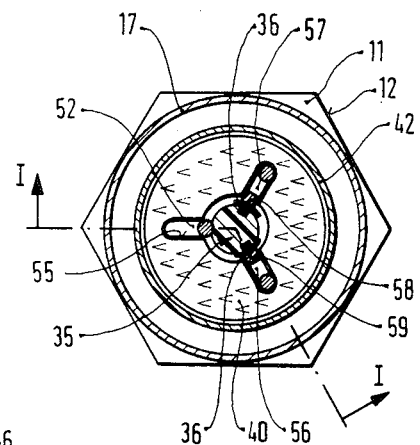

ELECTROCHEMICAL GAS SENSOR PROBE CONSTRUCTION

This invention concerns an electrochemical sensing probe to determine the oxygen content of exhaust gases of an engine, having a casing with means for mounting it in the wall of a pipe in which the gas to be measured flows and holding fast, in a gas-tight manner, a tubular closed-end sensor element projecting into the pipe with which a rod-shaped component is associated. The rod-like component acts like a heating element and extends up through the casing to carry contact areas cooperating with contact elements.

A sensing probe of a kind just described is shown in U.S. Pat. No. 4,155,827, but this probe has an inconveniently large length dimension, because its rod-like element associated with the sensor element, which carries a heater element, extends far out of the probe casing exteriorly of the pipe and has an electrical connection at its end where the connecting cable can easily be separated from the probe as the result of tugging, twisting or shaking stresses.

It has already been proposed that the contact areas of the conducting paths of sensor elements in the shape of small plates should provide electrical connection by laterally spring-pressed contact elements, but the manufacture of the parts of the connection regions of the sensor and their mounting in such a case is troublesome and expensive for mass production.

SUMMARY OF THE INVENTION

It is an object of the present invention to provide a sensor probe for determining oxygen content of engine exhaust gases of a relatively small longitudinal dimension in which the parts relating to the connection areas can be simply manufactured and assembled and, furthermore, will allow no electrical interruption in the contact region of the sensor probe as the result of pulling, twisting or shaking stresses.

Briefly, there are provided within the probe at least one spring contact element and at least one positioning element of the rod-shaped component, as well as the contact areas of the rod-shaped component. Each spring contact element, connected to a lead wire, is set in a cavity of an insulating part and is provided with a portion bent over in Z or wavy shape, which is supported in an electrically insulating manner on a shoulder facing the interior of the exhaust gas pipe. Each spring contact element is also supported in an electrically insulating manner by a stop surface of the probe which faces away from the sensor element.

This construction has the advantage of permitting a relatively short length dimension and an improved securing of the lead wires to the contact elements. This construction is also very suitable for use with oxygen sensor elements in the form of a solid electrolyte tube closed at its tip projecting into the exhaust gas pipe. The construction of the invention has the further advantage that a simple and effective securing of the rod-shaped component against undesired twisting is made possible.

BRIEF DESCRIPTION OF THE DRAWING

Further details of the sensor probe construction according to the invention are illustrated by way of example with reference to the annexed drawing, in which:

FIG. 1 is a longitudinal section of a gas sensor probe according to the invention on a magnified scale in the plane indicated by the section line I—I in FIG. 2, and FIG. 2 is a cross-section through the sensor probe passing through the line II—II of FIG. 1.

DESCRIPTION OF THE ILLUSTRATED EMBODIMENT

The sensor probe 10 shown in FIGS. 1 and 2 of the drawing has a metallic casing 11 that has an exteriorly hexagonal portion 12 and screw threading 13 as attachment means for building the device into a pipe, not shown in the drawing, through which flows a gas to be measured by the probe. A ring-shaped seal element 14, which is laid captively in a ring groove 15 between the hexagonal portion 12 and the screw threading 13, serves to seal the casing in the pipe. In the exterior end section of the casing 11 (exterior and interior refer to the exterior and interior of the unshown pipe), another ring groove 16 is provided which serves for crimping-on a closure shell 17 that prolongs the casing 11. This closure shell 17, which at its exterior end has a floor 18 pierced by a central opening 19, is fixed in place by means of several crimping indentations 20 in the ring groove 16.

The casing 11 has a longitudinal bore 21 having a shoulder 22 that faces away from the measuring end of the probe 10 and carries a ring-shaped seal element 23. A sensor element 24 lies with its head 25 against the shoulder 22 and its seal element.

The sensor element 24 in the present example is an oxygen measuring sensor, such as is known from German Utility Model 81 01 584, which is preferably used for the measurement of oxygen partial pressure in exhaust gases. This sensor element 24 has a solid electrolyte tube 26, the interior end section of which is closed off by a floor 27. On its outer surface exposed to the gas to be measured, it has a gas-permeable layer-like measuring electrode 28 and on its surface facing its interior cavity 29, it carries a layer-like gas-permeable reference electrode 30 that is exposed to a reference gas (e.g. air). While the measurement electrode 28 is in contact, through the ring-shaped seal element 23 with the casing 11 that is at ground or chassis potential, the reference electrode 30 preferably leads from the interior surface of the floor 27 of the sensor element all the way to the end surface 31 of the solid electrolyte tube 26, which is remote from its closed tip and the gas to be measured. For increasing the service life of the measurement electrode which consists mostly of a thin platinum layer, that electrode is coated with a protective layer (not shown) which is gas-permeable and consists, for example, of magnesium spinel.

The part of the sensor element 24 that protrudes out of the lengthwise bore 21 of the casing 11 towards the interior of the gas pipe is spaced from and surrounded by a protective tube 32 which has openings 33 for the admission and discharge of gas to be measured and is fixed at the measurement gas end of the casing 11 by crimping 34 or the like. This protective tube 32 serves to prevent the great temperature changes that arise in the gas to be measured and also particles contained in the measurement gas from directly affecting the sensor element 24 and leading to damage.

The interior chamber 29 of the sensor element 24 is substantially filled by the presence of a rod-shaped component 35 which also extends out of the sensor element 24 beyond the open end of the latter. This rod-shaped part 35 carries an electrical heating element, whose windings (not shown) are disposed in the end portion towards the closed end of the sensor element so that the portion of the sensor element 24 protruding out of the casing 11 will be heated thereby. The heating windings are preferably formed as conducting paths which are continued up to the cylindrical surface of the exterior end portion of the rod-shaped part 35 for their electrical connections where they are broadened into contact areas 36. The conducting path heater windings and the conductor paths (not shown) leading from them to the contact areas 36 are covered with thin electrical insulation (not shown). The rod-shaped part 35 terminates at its exterior end portion within the region surrounded by the closure shell 17 and is equipped with a positioning element 37 which assures the setting of the rod-shaped part 35 in its correct position. In the illustrated example, a groove in the outer surface of the exterior portion of the rod-shaped part 35 is provided as the indexing or fixing element 37 of the rod. Such a heating element is known in principle from U.S. Pat. No. 4,035,613 and it differs from the rod-shaped part 35 in essence only by the fact that an electrical connection is provided at each end, instead of having two connection areas 36 at a single end portion of the part.

On the end surface 31 of the open end of the sensor element 34, on which the reference electrode layer 30 terminates, there is placed a ring-shaped contact part 38 which surrounds the rod-shaped part 35 coaxially and clamps the rod-shaped part 35 fast in place by means of a collar 39 extending away from the sensor element 24. The collar 39 of this contact part 38 is provided with longitudinal slots (not shown in the drawing) which are open at their end away from the sensor element 24.

In the space bounded by the sensor element 24, the casing 11 and the closure shell 17, two insulating sleeves 40 and 41 are located. These are preferably made of a ceramic material (e.g. aluminum oxide) and are held coaxially in the gas sensor sonde 10 by means of a guide sleeve 42. The latter is held at its end towards the measurement gas (e.g. by a press-fit or by caulking) in the longitudinal bore 21 of the casing 11 and has at its other end an outwardly directed flange 43 which extends laterally almost to the closure shell 17. The annular space 44 between this guide sleeve 42 and the closure shell 17 functions as a barrier against moisture which can enter into the probe 10 with the air serving as reference gas in the region between the lower end of the closure shell 17 and the casing 11. Between the flange 43 of the guide sleeve 42 and the floor 18 of the closure shell 17, a ring-shaped spring element (disc or cup spring) 45 is disposed, which lies against the floor 18 of the closure shell 17 on one hand and lies, on the other hand, under mechanical bias, on a coaxial step 46 of the insulating sleeve 40. As a result of the mechanical bias of this spring 45, the first insulating sleeve 40 presses with its end surface 47 against an oppositely facing ring step 48 of the second insulating sleeve 41 and, consequently, presses the end surface 49 of the second insulating shell 41 against the contact part 38 which is electrically connected with the reference electrode 30.

The second insulating sleeve 41, by means of its central bore 50, surrounds the rod-shaped part 35 that operates as a heating element, and near one end of that bore surrounds and holds the collar 39 of the contact part 38. A wire conductor 52 passes along the groove 51 running parallel to the longitudinal bore 50 of the second insulating sleeve 41 and is fastened at its end to the contact part 38 in some well-known way (e.g. by spot-welding). The other end of this wire 52 is led through a bore 53 running longitudinally through the first insulating sleeve 40 and extends out of the latter somewhat. In its mid-portion, the wire 52 has an undulating deviation 54 which is laterally held and positioned in a cavity 55 of the first insulating sleeve 40 directed radially with respect to the axis of the probe 10. The wire 52, with a portion of its deviation extending towards the axis of the probe 10 dips into the indexing configuration 37 in the end portion of the rod-shaped part 35 remote from the sensor element 24. As already mentioned, this indexing configuration 37 is preferably constituted as a longitudinal groove on the rod-shaped part 35 and serves to secure the rod-shaped part 35 against rotation.

There are two supplementary cavities 56 and 57 in the first insulating sleeve 40 which likewise run radially, facing the axis of the probe 10 and serve for the respective positioning of two spring contact elements 58 and 59. In order to show these in the drawing more clearly, the section shown by FIG. 1 is a section that runs as shown by the section line I—I of FIG. 2 (the section is in two planes that intersect on the axis of the probe).

The first insulating sleeve 40 is provided with passage holes 60 respectively for the end sections of the wire-spring connection elements 58 and 59. These holes, at their ends towards the sensor 24, communicate with the corresponding cavities 56 and 57. Each hole 60 has got a shoulder 61 facing in the direction of the sensor element 24.

The exterior end portions of the wire-spring connection elements 58 and 59 protrude out of the first insulating sleeve 40 towards the exterior end of the probe. The portions of the wire-spring connection elements 58 and 59 extending in the other direction out of the holes 60 of the first insulating shell 40 are located in the respective slot-like cavities 56 and 57 of the first insulating sleeve 40 and are bent in Z-shape outward from the probe axis and lie with this Z-shaped deviation 62 against a shoulder 61 in the first insulating sleeve 40. These Z-shaped bends 62 of the wire-spring elements 58 and 59 serve for securing against pull, twist or shaking stresses which may originate in the connection cable 63 with its connection wires 64/1 and 64/2. The end portions of the connection wires 64/1 and 64/2 are connected with the end portions of the reslient connection elements 58 and 59 projecting out of the first insulating sleeve 40 by crimping, welding and/or soldering with the use of connection sleeves 65. The end portion of the wire 54 protruding out of the first insulating sleeve 40 is connected with the connection wire 64-3 of the connection cable 63, also with a similar connection sleeve 65.

Each of the Z-shaped deviations 62 of the resilient connection elements 58 and 59, at its end towards the gas to be meassured, runs at an offset all the way to a stop surface 66 which is formed by an end surface of the second insulating sleeve 41.

The resilient contact elements 58 and 59 are formed with hairpin loops, the vertices of which lie against the stop surfaces 66 of the second insulating sleeve 41 and then lead back, in the direction of the outer end of the probe 10, to the respective Z-shaped bends 62 of the resilient wires 58 and 59. The respective free ends of the hairpin loops are each bent slightly but sharply at 67, where they lie under mechanical bias against the corresponding contact area 36 of the rod-shaped part 35. In the region of the bend 67, the cross-section of each resilient connection element 58 and 59 is preferably flattened in such a way that the pressure exerted between the respective ends 67 and the contact areas 36 leads to no damage of the contact areas 36.

Instead of a Z-shaped double bend 62, a more sinuous offsetting double bend can be used in order to secure the structure against tension or shaking stresses of the cable 63. It is furthermore, possible, in addition to the indexing element 37 in the rod-shaped part 35 already decribed, or instead of it, to provide positioning elements molded into the rod-shaped part 35 in the region of the contact areas 36 which likewise are suitable for holding the rod-shaped part 35 against being twisted out of position.

The ends of the connection sleeves 65 and also the end portion of an elastic insulating plug 69 preferably stand on the end surface 68 of the first insulating sleeve 40. The plug 69 surrounds the connection shell 65 and parts of the connection wires 64/1 to 64/3 and holds them sealed fast in passage bores 70. The flange portion 71 of this insulating plug 69 surrounds the end portion of the first insulating sleeve 40 protruding through the opening 19 out of the closure shell 17 and its end surface 72 stands tight on the outer surface of the floor 18 of the closure sleeve 17. A tubular and preferably metallic cap sleeve 74 is preferably provided on the outer surface 73 of the insulating plug 69. The cap sleeve grips closely over the end portion of the closure shell 17 with its broadened end section and is fastened to the closure shell 17 by means of a few spot welds 75 or by other known fastening means. The cap sleeve 74 thus holds the insulating plug 69 under mechanical bias in the longitudinal direction of the probe 10.

It should be added that the described connection between the respective contact areas 36 of the rod-shaped part 35 and the resilient connection elements 58 and 59 is suitable not only for measurement probes 10 for the determination of oxygen partial pressure in gases and utilize a solid electrolyte tube. Such a connection can, all the more, find application in sensors in which a rod-shaped component protrudes out of a casing on the measurement gas side and carries a measuring element, as shown in FIG. 2 of U.S. Pat. No. 4,212,720.

It will thus be seen that although the invention has been described with reference to a particular illustrative embodiment, variations and modifications are possible within the inventive concept.

We claim:

1. Gas-content sensor probe having a casing (11) equipped with means for fastening said casing gas-tight in the wall of a pipe in which a gas to be measured flows, said casing having a central bore, said probe having a casing-extension shell (17, 74) extending from an extremity away from said pipe substantiallly to said casing and closed off at said extremity against entry of moisture and dirt, a tube-shaped sensor element (26) held at one end in said central bore of said casing and also a rod-shaped part (35) occupying most of the interior cavity of said sensor element with a portion of said rod-shaped part that on its surface carries a heating element and having at least two contact surface portions (36) in the region of the rod end remote from said sensor element, against which contact portions a plurality of resilient contact elements (58, 59) respectively bear under mechanical bias, and are connected with electrical connection lead wires for said probe, said rod-shaped part having at least one configuration feature for positioning against rotation.

said resilient contact elements (58, 59), said end and said contact portions of said rod-shaped part (35), and said at least one positioning configuration feature (37) of said rod-shaped part being located within the portion of said probe enclosed by said casing and said casing extension shell;

each of said resilient contact elements connected to said connection lead wires being a wire held in a cavity (56, 57) in a first insulating part (40) and provided with a portion (62) at one end of said cavity bent successively in opposite directions in substantially the same plane, said portion at least in part abutting on a first shoulder (61) facing said cavity (56, 57), each of said resilient wires also being bent, at another end of said cavity substantially in said same plane to provide a reversely bent wire end running along the surface of said rod-shaped part (35) for contact with one of said contact portions (36) thereof, and said reversely bent portions of said resilient wires being supported in an electrically insulating manner by abutment on a second shoulder (66) of a second insulating part (41) facing said first shoulder across said cavity and facing in the direction away from said sensor element, each of said resilient wires passing through said first insulating part in a guiding hole leading from said cavity (56, 57) to a place where the resilient wire protrudes from said first insulating part for connection, within an elastic insulating plug (69) that closes said extremity of said casing-extension shell, to one of said connection lead wires.

2. Sensor probe according to claim 1, in which the portions of said resilient connection wire elements (58, 59) which are located outside of said cavity (56, 57) run respectively through passage holes of said first insulating part (40) in which said cavities (56, 57) are provided and have extremities respectively projecting out of said holes and of said first insulating part (40), said first insulating part having the configuration of a first insulating sleeve.

3. Sensor probe according to claim 2, in which said second shoulder (66) is an end face of said second insulating part having a sleeve configuration and constituting a second insulating sleeve (41) which is interposed between said first insulating sleeve and said sensor element in abutment therewith.

4. Sensor probe according to claim 3, in which said casing extension shell includes a shell member (17) having an end wall (18) pierced by an opening serving for passage of an end of said first insulating sleeve (40) within which run said resilient connection wire elements, and in which a coaxially disposed biased spring element (45) bears against said pierced end wall and exerts axial force on said first insulating sleeve and thereby on said second insulating sleeve, as well as on said sensor element (26) and thereby on a seal element (23) interposed between said sensor element (26) and said casing (11) sealing the interior of the probe against entry of the gas being measured.

5. Sensor probe according to claim 1, in which said sensor element (26) is a solid electrolyte tube capable of conducting oxygen ions having a closed tip (27), having a measuring electrode (28) constituted as a gas-permeable layer exposed to the gas to be measured on the outside of said solid electrolyte tube and having on its interior surface a reference electrode (30) in the form of a gas-permeable layer exposed to a reference gas.

6. Sensor probe according to claim 5, in which said measuring electrode (28) is provided with a supplementary gas-permeable layer.

7. Sensor probe according to claim 5, in which said reference electrode (30) is electrically connected to a corresponding connection lead wire (64/3) by the interposition of a conductor wire (52) connected with a contact part (38) making contact with said reference electrode (30) on the end surface (31) of said solid electrolyte tube (26) remote from said closed tip (27) thereof.

8. Sensor probe according to claim 7, in which said conductor wire (52) connecting said reference electrode to said connection lead therefor has a portion bent out of line producing a lateral deviation (54) of said wire which seats in said positioning configuration feature (37) of said rod-shaped part.

9. Sensor probe according to claim 8, in which said deviation (54) of said conductor wire (52) connecting said reference electrode to said connection lead lies substantially in a plane oriented radially to the longitudinal axis of said probe.

10. Sensor probe according to claim 9, in which said positioning configuration feature (37) is a longitudinal groove in the periphery of said rod-shaped part (35).

11. Sensor probe according to claim 1, in which said portion bent successively in opposite directions of at least one of said resilient contact element (58, 59) seats in said positioning configuration feature of said rod-shaped part (35).

12. Sensor probe according to claim 11, in which said successively bent portion (62) of at least one of said resilient contact wire elements (58, 59) is bent in a plane oriented radially with respect to the axis of said probe (10).

13. Sensor probe according to claim 12, in which said positioning configuration feature (37) is a longitudinal groove in the periphery of said rod-shaped part (35).

* * * * *